US006653014B2

(12) United States Patent
Anderson et al.

(10) Patent No.: US 6,653,014 B2
(45) Date of Patent: *Nov. 25, 2003

(54) POWER SOURCES FOR IONTOPHORETIC DRUG DELIVERY SYSTEMS

(75) Inventors: Carter R. Anderson, Inver Grove Heights, MN (US); Clayton J. Anderson, Burnsville, MN (US); Lori A. Grace, Lino Lakes, MN (US); Russell L. Morris, Lindstrom, MN (US)

(73) Assignee: Birch Point Medical, Inc., Oakdale, MN (US)

( * ) Notice: Subject to any disclaimer, the term of this patent is extended or adjusted under 35 U.S.C. 154(b) by 317 days.

This patent is subject to a terminal disclaimer.

(21) Appl. No.: 09/867,949

(22) Filed: May 30, 2001

(65) Prior Publication Data

US 2002/0182485 A1 Dec. 5, 2002

(51) Int. Cl.[7] .................. H01M 2/28; H01M 6/00; H01M 10/00; C04B 35/00; A61N 1/30; A61M 25/00; A61M 5/32

(52) U.S. Cl. .............. 429/122; 429/123; 264/104; 264/105; 604/20; 604/21; 604/265

(58) Field of Search .................. 429/122, 123, 429/137; 264/104, 105, 108, 209; 604/20, 21, 265

(56) References Cited

U.S. PATENT DOCUMENTS

| 116,562 A | 7/1871 | Collins |
|---|---|---|
| 175,974 A | 4/1876 | Hall |
| 222,276 A | 12/1879 | Hunter |
| 385,556 A | 7/1888 | Hoke |
| 393,741 A | 12/1888 | Collins |
| 770,014 A | 9/1904 | Linn |
| 857,664 A | 6/1907 | Overman |
| 4,619,252 A | 10/1986 | Ibbott |
| 4,713,050 A | 12/1987 | Sibalis |
| 4,722,726 A | 2/1988 | Sanderson et al. |
| 4,767,401 A | 8/1988 | Seiderman |

(List continued on next page.)

FOREIGN PATENT DOCUMENTS

| DE | 1967927 | 7/1934 |
|---|---|---|
| DE | 2 263 792 | 3/1974 |
| EP | 0 060 451 | 3/1982 |
| EP | 0 308 572 | 8/1984 |
| EP | 456 122 | 5/1991 |
| EP | 0 893 139 | 7/1998 |
| FR | 2 263 792 A | 10/1975 |
| GB | 410009 | 5/1934 |
| GB | 2 206 493 | 1/1989 |
| GB | 0456122 | 11/1995 |
| WO | WO 01/49365 | 7/2001 |

OTHER PUBLICATIONS

"Transdermal Iontophoresis. Part I: Basic Principles and Considerations", Vinod Nair, Omathanu Pillai, Ramarao Poduri and Ramesh Panchagnula, *Methods Find Exp Clin Pharmacol*, 1999, 21(2): 139–151.

"Iontophoresis: Applications in Transdermal Medication Delivery", Charles T. Costello, Arthur H. Jeske, *Physical Therapy*, vol. 75, No. 6, Jun. 1995, pp. 554–563.

*Primary Examiner*—Bruce F. Bell
*Assistant Examiner*—Donald V. Scaltrito
(74) *Attorney, Agent, or Firm*—Nikolai & Mersereau, P.A.; C. G. Mersereau (57) ABSTRACT

The capacity of an electro-chemical power source having an initial amount of an oxidizable material and an initial amount of a reducible material, is adjusted to a target capacity by altering the initial amount of one or both of the oxidizable material and the reducible material available to participate in the source by a technique selected from the group consisting of adding, removing and isolating a known fraction of the initial amount from the power source.

59 Claims, 7 Drawing Sheets

U.S. PATENT DOCUMENTS

| | | | |
|---|---|---|---|
| 4,927,408 A | | 5/1990 | Haak et al. |
| 5,162,042 A | | 11/1992 | Gyory et al. |
| 5,162,043 A | * | 11/1992 | Lew et al. .................... 604/20 |
| 5,203,768 A | | 4/1993 | Haak et al. |
| 5,221,254 A | | 6/1993 | Phipps |
| 5,254,081 A | | 10/1993 | Maurer et al. |
| 5,295,979 A | | 3/1994 | DeLaurentis et al. |
| 5,298,017 A | | 3/1994 | Theeuwes et al. |
| 5,320,731 A | | 6/1994 | Muller et al. |
| 5,322,520 A | | 6/1994 | Milder |
| 5,326,341 A | * | 7/1994 | Lew et al. .................... 604/20 |
| 5,354,321 A | | 10/1994 | Berger |
| 5,356,632 A | | 10/1994 | Gross et al. |
| 5,358,483 A | | 10/1994 | Sibalis |
| 5,403,275 A | | 4/1995 | Phipps |
| 5,405,317 A | | 4/1995 | Myers et al. |
| 5,431,625 A | | 7/1995 | Fabian et al. |
| 5,458,569 A | | 10/1995 | Kirk, III et al. |
| 5,464,387 A | * | 11/1995 | Haak et al. .................... 604/20 |
| 5,466,217 A | | 11/1995 | Myers et al. |
| 5,533,971 A | | 7/1996 | Phipps |
| 5,605,536 A | | 2/1997 | Sibalis |
| 5,651,768 A | | 7/1997 | Sibalis |
| 5,685,837 A | | 11/1997 | Horstmann |
| 5,725,817 A | * | 3/1998 | Milder ....................... 264/104 |
| 5,759,564 A | * | 6/1998 | Milder et al. ............... 424/426 |
| 5,772,688 A | | 6/1998 | Muroki |
| 5,983,130 A | | 11/1999 | Phipps et al. |
| 6,421,561 B1 | * | 7/2002 | Morris ....................... 604/20 |

* cited by examiner

POWER SOURCES FOR IONTOPHORETIC DRUG DELIVERY SYSTEMS

BACKGROUND OF THE INVENTION

I. Field of the Invention

The present invention is related generally to transdermal delivery of therapeutic agents by the use of an applied electro motive force (emf), commonly known as iontophoresis. More particularly, the present invention is directed to a process for preparing single-use power sources for use in disposable, wearable forms of iontophoretic delivery devices and the power sources made by the process.

II. Related Art

The process of iontophoresis was described by LeDuc in 1908 and has since found commercial use in the delivery of ionically charged therapeutic agent molecules such as pilocarpine, lidocaine and dexamethasone. In this delivery method, ions bearing a positive charge are driven across the skin at the site of an electrolytic electrical system anode, while ions bearing a negative charge are driven across the skin at the site of an electrolytic system cathode.

Earlier, and some present, iontophoretic devices have been typically constructed of two electrodes attached to a patient, each connected by a wire to a remote power supply, generally a microprocessor-controlled electrical instrument. Because they involve direct patient contact with the electrodes, these devices are most conveniently constructed so as to make use of disposable electrodes, associated with a reusable electric instrument. The electrical instruments generally are battery powered and designed in a manner such that the batteries can be easily replaced as they become consumed.

More recently, self-contained wearable iontophoretic systems have been developed. These systems are advantageous in that they do not have external wires and are much smaller in size. Examples of such systems can be found in a variety of U.S. patents, including U.S. Pat. Nos. 4,927,408; 5,358,483; 5,458,569; 5,466,217; 5,533,971; 5,605,536; 5,651,768; and 5,685,837.

Depending on factors relating to cost, particular use and convenience, wearable iontophoretic systems can be "reusable" or "disposable". Reusable systems may be defined as systems in which the power source is designed to be replaceable; whereas disposable systems may be defined as devices in which the entire iontophoretic system is designed to be disposed following a single use or consumption of the original power source.

The power sources for self-contained iontophoretic systems can further be characterized as "galvanic", "electrolytic" or a combination of these. "Galvanic" power is defined as power supplied by a couple, including a pair of electrodes having amounts of dissimilar surface electroactive materials that inherently provide a voltage difference between the electrodes (anode and cathode) and which normally are connected directly by a conductor. "Electrolytic" power sources are power sources generally remote from but in conductive contact with the electrodes, and usually include such devices as button-type batteries or sheet-like multi-layer elements. Electrolytic and galvanic sources of power are known in the art and describe, for example, in the above-referenced U.S. Pat. Nos. 4,927,408; 5,533,971; and 5,685,837.

With iontophoresis, the rate that medications are introduced is a function of the level of current, while the total quantity of medication delivered is a function of both current level(s) and time or the amount of total charge transferred. Because of this relation, often the quantity of medication introduced by iontophoresis is referred to in units of mA-minutes of dosage. Thus, for example, an equivalent 40 mA-minute dosage can be delivered at different rates; 0.1 mA for 400 minutes, 1 mA for 40 minutes, 10 mA for 4 minutes, etc.

Control of the dosage delivered by iontophoresis is usually accomplished by means of electrical circuitry in the form of electrical components mounted on the circuit layer. Electrical components can be utilized to regulate the level, waveform, timing and other aspects of the electrical current and the system usually includes a microprocessor adapted to control the current over time. These electrical circuits are well known and are described, for example, in U.S. Pat. No. 5,533,971.

Recently, means have been developed to regulate the total iontophoretic dosage in its delivery-time profile by precise, pre-determined control of the charge capacity of the power supply design. In this regard, reference is also made to certain other pending U.S. patent applications assigned to the same assignee as the present application. These include application Ser. No. 09/674,211, filed Oct. 26, 2000, entitled "CONTROLLED DOSAGE DRUG DELIVERY SYSTEM", and application Ser. No. 09/613,984, filed Jul. 11, 2000, entitled "RATE ADJUSTABLE DRUG DELIVERY SYSTEM". Both of these references deal with aspects of galvanic devices and disclose power supply designs that alone regulate iontophoretic delivery to a known, pre-determined total dosage. The systems eliminate the need for microprocessors and current control circuitry. The contents of both of these applications are deemed incorporated by reference herein for any purpose.

Although wearable, disposable systems have demonstrated a great convenience advantage, they must also incorporate high flexibility to be functionally effective; and they must be low enough in cost to be economically effective. Generally, as the size and number of components increase, the systems become less desirable as wearable systems and costs also increase. Therefore, it is a desirable goal to reduce the complexity of these devices and to design wearable systems with a minimal number of components, particularly components that can be readily mass-produced.

It is well known in manufacturing piece parts that costs are reduced by production in high volume, typically batch (or lot) quantities. However, it has been discovered that mass production of iontophoretic power supplies to affixed, pre-determined charged dosage within close tolerances is difficult to accomplish. In producing large batch quantities, there inevitably exists variability associated with the manufacturing process. Thus, for example, the actual capacity of power supplies produced and so the associated dosage produced in a manufacturing lot often deviates somewhat from the capacity intended (or "target") dosages. This is not totally unexpected inasmuch as iontophoretic devices of the class are generally designed to optimally deliver a fixed and known charge in a range between about 0.06 and 60 coulombs, which corresponds to between 0.00000062 and 0.00062 gram equivalent weights of oxidizable or reducible species in limiting supply. Clearly, consistency at these low amounts is a challenge.

Additionally, it has been discovered that drift can occur during processing to cause a segment of a lot to deviate from the rest. For example, in building a sequence of parts which constitute a manufacturing lot, nominally between 1,000 and 1,000,000 parts, a first portion of the lot may deviate from a middle or end portion. Even when several devices are prepared in a single manufacturing step, deviations can occur between groupings.

Thus, it would be desirable to achieve a manufacturing process which can overcome such manufacturing deviations and result in power supplies of increased manufactured consistency.

SUMMARY OF THE INVENTION

The present invention provides improved process for the preparation of power sources intended to be used in iontophoretic delivery systems that are disposable, wearable and constructed so as to provide a pre-determined, known iontophoretic charged dosage. The benefits provided by the methods described by this invention make possible the production of more consistent power sources in high manufacturing volumes, thereby reducing costs. By means of this invention, a method is provided for characterizing the "actual" charged dosage for a production lot of iontophoresis power supplies, intended to be built to a pre-determined "target" charged dosage. Power sources can be independently used or designed to be a component along with other electrical circuitry. In the process, a test characterization is conducted on a selected sampling of a lot which furnishes results that can be extrapolated to the entirety of the lot. Methods of test characterization are provided for both electrolytic and galvanic power sources to be used in such devices.

The invention further provides a method for adjusting the capacity of iontophoretic power sources so as to make them conform to an acceptable range of charged dosage capacities. Thus, if after a lot characterization, it is determined that all or a portion of the manufactured lot fall outside of accuracy or precision specifications, the second aspect of this invention provides means to render that lot (or portion thereof) conforming to those specifications. This can involve either an increase or decrease in such capacity.

The invention also contemplates galvanic or electrolytic power sources of pre-determined charged dosage capacity and wearable iontophoretic devices which incorporate them.

Whereas a limited number of examples are utilized, it will be understood that these are meant to exemplify one or more aspects of the invention rather than to limit its scope and variations will occur to those skilled in the art upon familiarization with the specification, drawings and claims appended hereto.

BRIEF DESCRIPTION OF THE DRAWINGS

In the drawings, wherein like numerals are utilized to designate like parts throughout the same.

DETAILED DESCRIPTION

The detailed description of the present invention illustrates the principles, characterization and manipulation of capacity in advanced power sources used in iontophoretic drug delivery systems. As previously stated, the application of the principles encompassed by the present inventive concept, however, are much broader and, in reality, a great number of configurations and procedures of the concept are possible. Thus, while the power sources disclosed may be particularly well suited to iontophoresis, other uses for such devices are also contemplated. Accordingly, the descriptions and accounts given herein are intended as examples and not limitations.

Figure 1A:
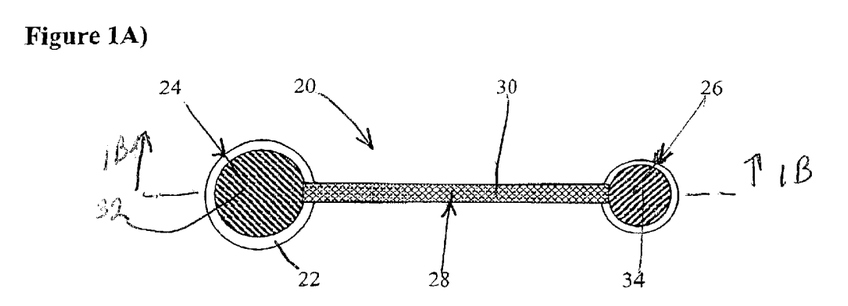
FIGS. 1A and 1B are schematic top and cross-sectional drawings of an example of a galvanic power source in accordance with the invention.
Figure 1B:
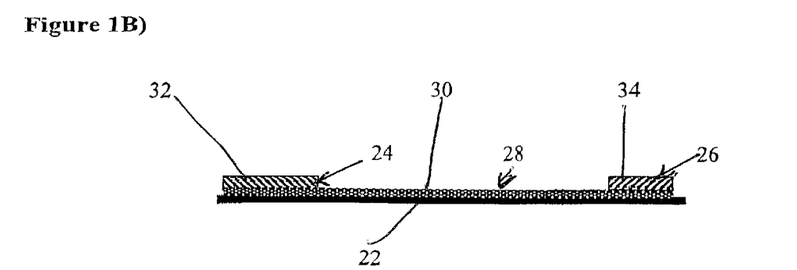
Figure 9:
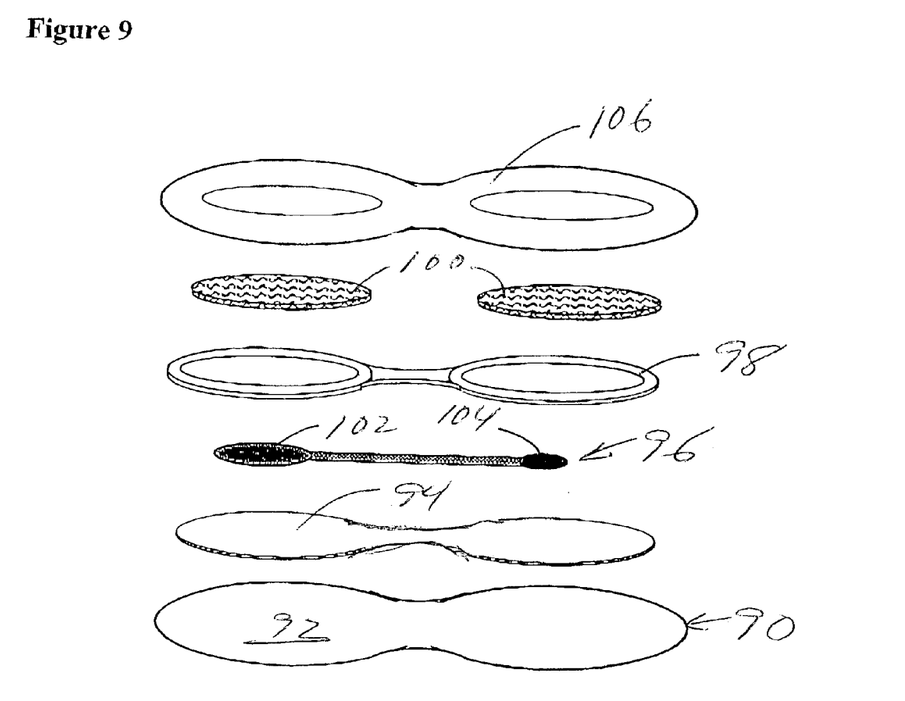
FIG. 9 is an exploded view disclosing a possible assembly arrangement of a wearable iontophoretic patch utilizing a power source in accordance with the present invention.
Figure 10:
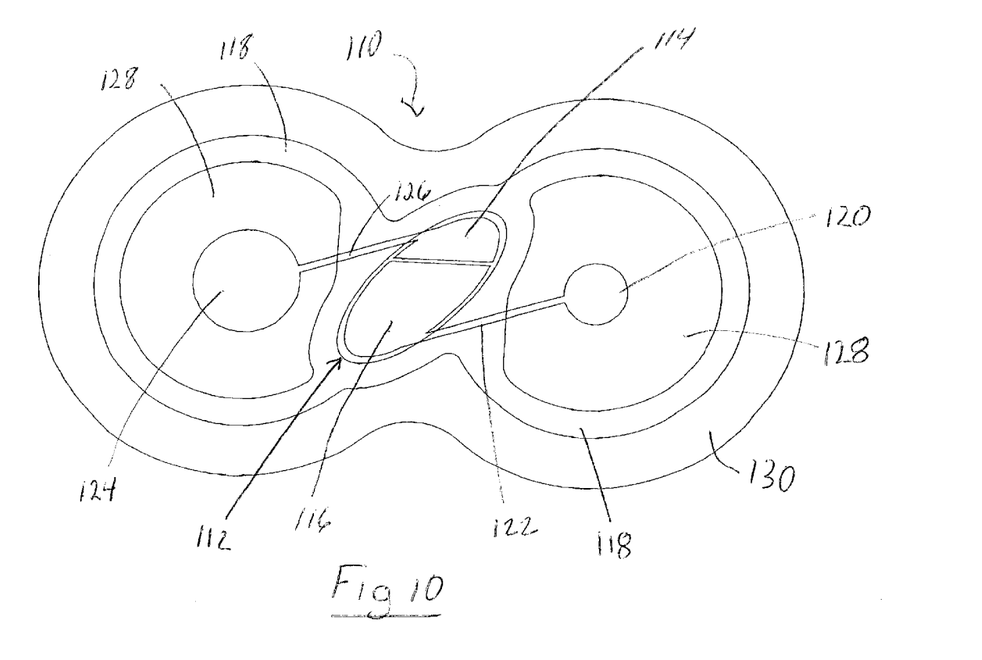
FIG. 10 is a schematic view depicting a hybrid multiple-couple power source in accordance with the invention as contained in a wearable iontophoresis patch.

FIGS. 1A and 1B are schematic representations of a galvanic power source, generally at 20, for use in a wearable iontophoretic device such as illustrated in FIGS. 9 and 10. FIG. 1A represents the power source in top view and FIG. 1B depicts a side elevational cross section of the device of 1A. The power source includes a flexible non-conductive support or substrate layer 22 defining electrodes 24 and 26 and an intermediate portion 28 and capable of carrying a variety of conductive over-layer materials such as the layer of conductive material 30, which may be a printed layer of silver paste. Electrode 24 is characterized by a top layer of electroactive reducible material 32 such as AgCl paste printed over a pre-determined portion of the conductive material 30. Electrode 26, shown as an area slightly smaller than electrode 24, is constructed using a layer of electroactive oxidizable material species 34, such as Zn paste printed over a different section of pre-determined area of the conductive material 30. When Zn and AgCl materials are used as electroactive species, a 1-volt potential is generated between electrodes 24 and 26, with a coulombic capacity dictated by the minimum quantity (in equivalent weight) of Zn and/or AgCl used.

Figure 2:
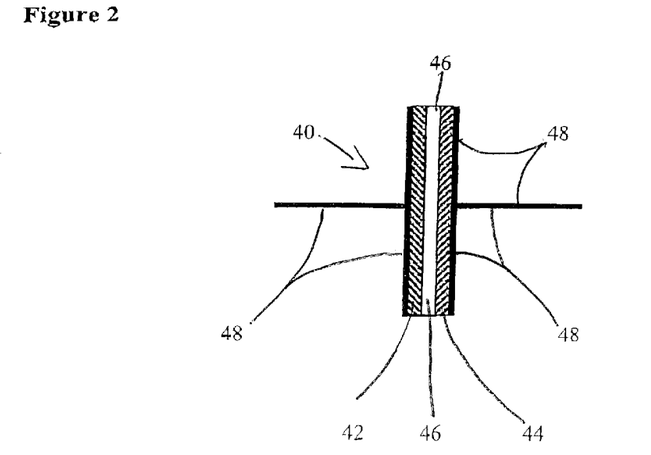
FIG. 2 is a schematic cross-sectional representation through an example of an electrolytic power source in accordance with the invention.

In FIG. 2, an electrolytic power source is depicted generally at 40 in which a reducible species 42 is separated from oxidizable species 44 by an electrolyte layer 46. Electrolyte layer 46 is tonically conductive, and is typically constructed by the incorporation of inorganic salts, such as ammonium chloride, into a porous support matrix. An electrically conductive layer 48 serves to connect the power source to separate electrodes (not shown). As with the galvanic power supply, the voltage generated by the power source is directly related to the oxidizable and reducible species selected, and the coulombic capacity dictated by the minimum quantity of oxidizable and/or reducible species (in equivalents) present. It will also be that additional layers of oxidizable and reducible species may be alternated in serial sandwich construction in the manner of the layers shown in order to increase the potential of the electrolytic power source. The cell stacking technique is considered within the knowledge of those skilled in the art and can be used in an embodiments incorporating the principals of the present invention.

The power sources of the present invention may be fabricated by conventional means using paste type materials in conjunction with well known screen printing and baking processes. While this enables generally accurate layer thicknesses to be produced, the results can vary somewhat from batch to batch and also across the area of the same batch. Thus, as discussed above, though the power sources are intended to be built to a particular capacity, it is generally necessary to test samples to characterize and verify actual coulombic capacity of the power sources when manufactured in lot quantities.

Figure 3A:
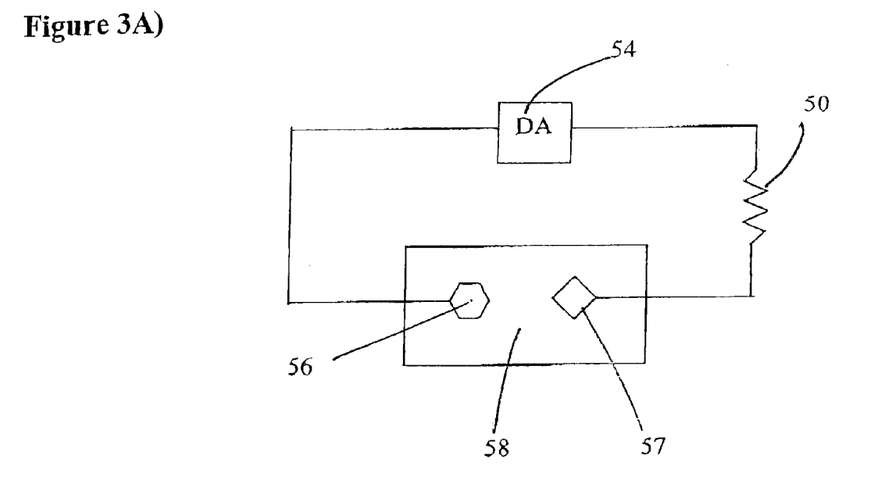
FIGS. 3A and 3B are schematic representations of galvanic power source test circuitry, FIG. 3A being configured for a direct measurement of the current produced by a power source as it discharges across a resistor and FIG. 3B, for an indirect measurement of the current produced by a power source by measuring the voltage drop across a resistor.
Figure 3B:
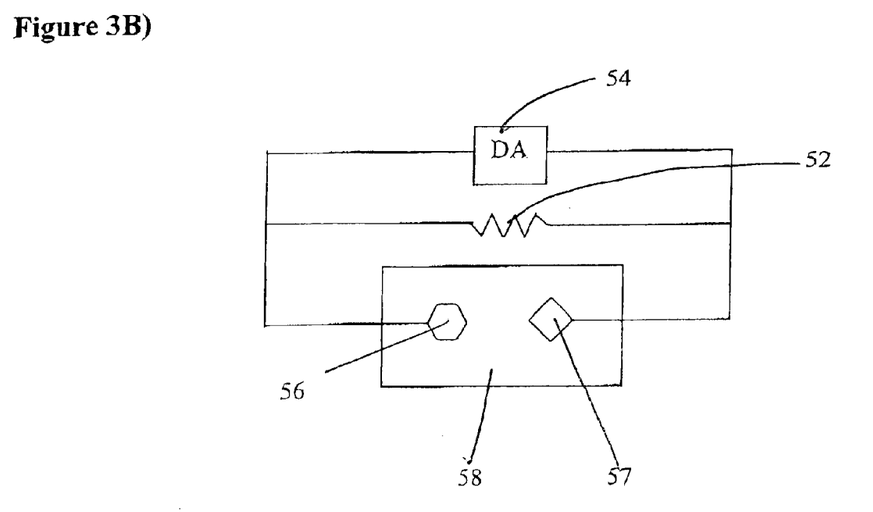

FIGS. 3A and 3B depict schematics of test fixtures for use with a galvanic power source, using series and parallel resistors 50 and 52, respectively. A data acquisition station 54, is used to measure current flow as a function of time, and is typically a combination of an ammeter or voltmeter, software and computer station. Electrode 56 represents an oxidizable electrode to be tested and electrode 57 represents a reducible species electrode to be tested. For evaluation only of oxidizable electrodes of a given lot, electrode 57 may be a "dummy" electrode having an excess reducible species coulombic capacity. For evaluation of only reducible electrodes of a given lot, electrode 56 may be a "dummy" electrode having an excess oxidizable species coulombic capacity. Interconnection means 58 is provided and is typically an ionically conductive aqueous solution, such as provided by emersion of oxidizable and reducible electrodes in a 1%–10% solution of sodium chloride. Resistor 50 is optional and serves to reduce or limit the level of current (thereby increasing discharge time) if desired. For indirect measurements of current flow, resistor 52 must be of known resistance so as to ascertain current flow from the voltage across the resistor 52 by an Ohm's Law relationship. Total coulombic capacity is determined by the integrated quantity of current over time, from the time of initial current flow until the battery capacity is fully consumed.

Figure 4A:
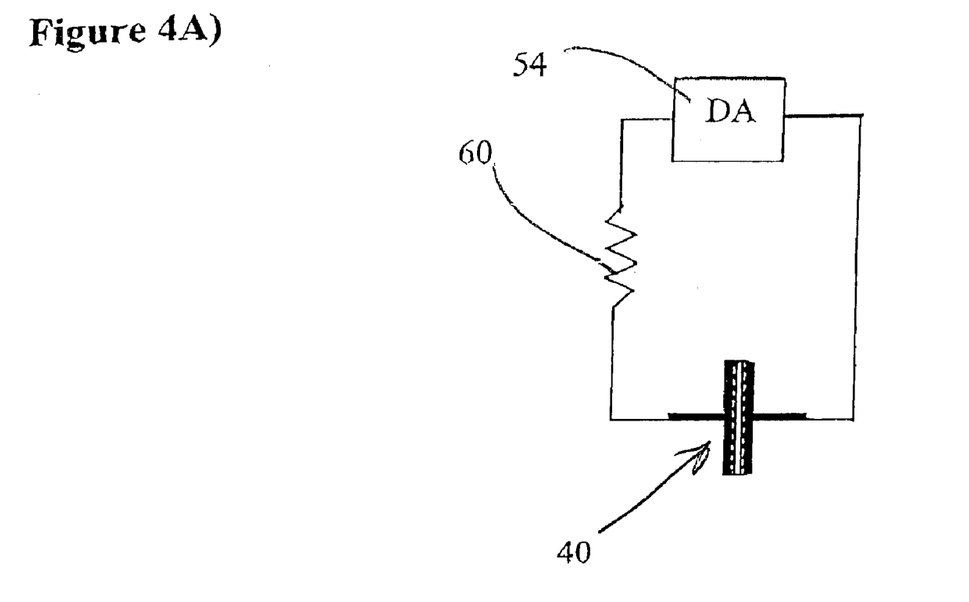
FIGS. 4A and 4B are schematic representations of electrolytic power source test circuitry, FIG. 4A being configured for a direct measurement of the current produced by a power source as it discharges across a resistor and FIG. 4B, for an indirect measurement of the current produced by a power source by measuring the voltage drop across a resistor.
Figure 4B:
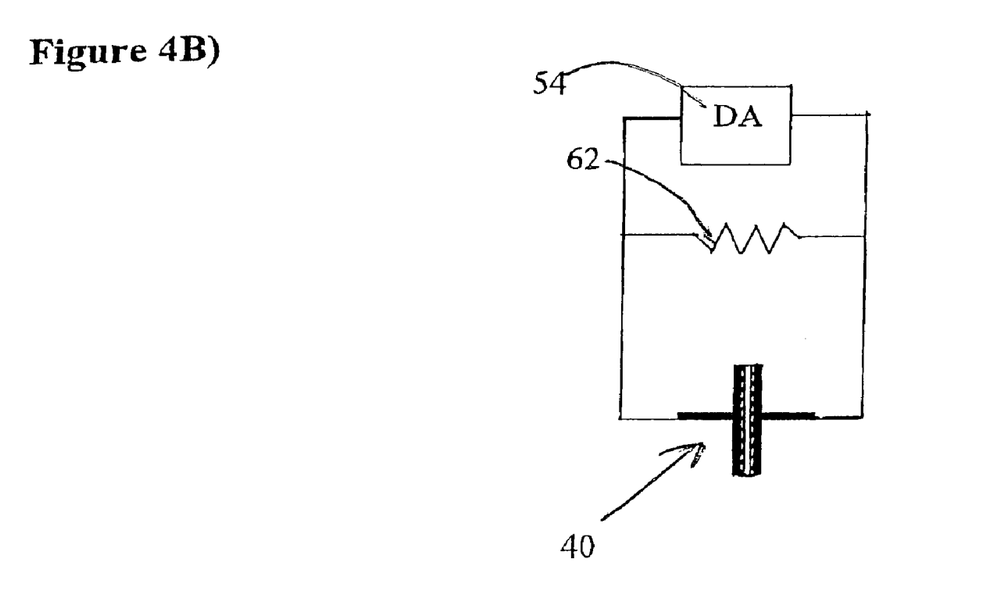

Testing of electrolytic power sources may be accomplished in fixtures such as depicted in FIGS. 4A and 4B. The multi-layer power source structure 40 containing both oxidizable and reducible species is evaluated by data acquisition device 54 by measurement of current flow, as with the devices of FIGS. 3A and 3B, in a circuit optionally containing a series connected resistor 60 (FIG. 4A) or the voltage across parallel connected resistor 62 (FIG. 4B). As with the testing of galvanic power sources, total coulombic capacity is determined by the integrated quantity of current over time using data acquisition station 54, from the time of initial current flow until the time at which battery capacity is fully consumed.

From a statistical sampling of power sources from manufactured lots, average coulombic capacity can be determined for the lot, as well as such statistical measures as range, standard deviation, drift, etc. From this comparison, it can be determined whether or not the lot requires further processing for it to fall within desired specifications. If the measured average coulombic capacity deviates from the "target" coulombic capacity; all or a selected portion of that lot can be further processed as described below.

Figure 5A:
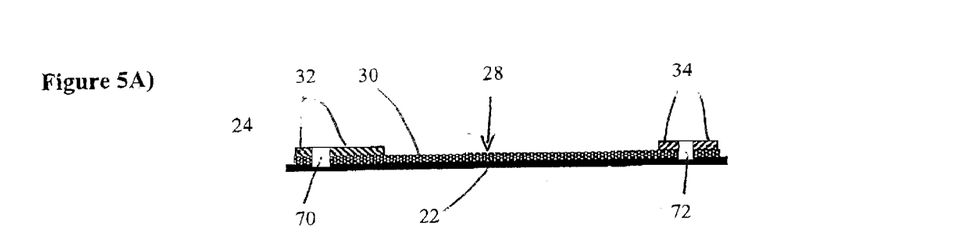
FIGS. 5A and 5B are respective cross-sectional and top views of one embodiment for adjusting the capacity of a galvanic power source.
Figure 5B:
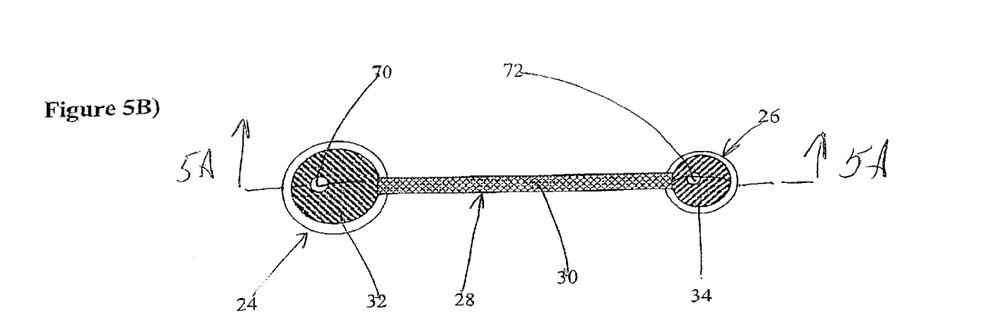
Figure 6A:
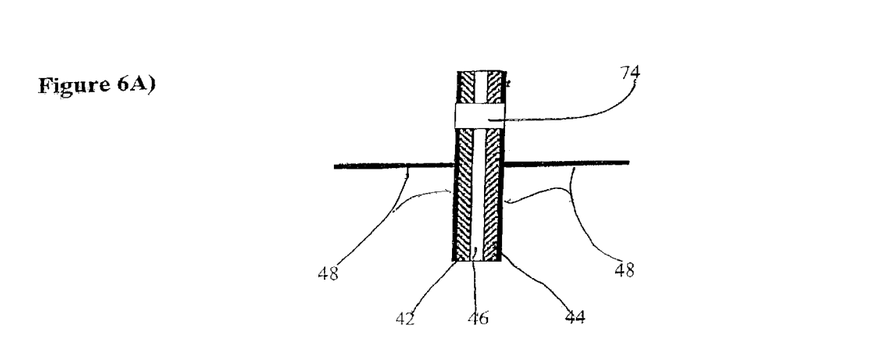
FIGS. 6A and 6B respectively illustrate cross-sectional and plan views showing the adjustment of the capacity of an electrolytic power source.
Figure 6B:
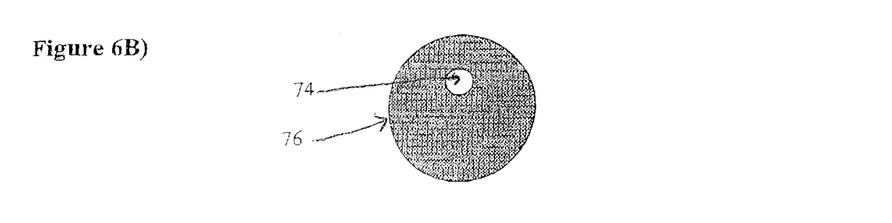

If the measured lot capacity exceeds that desired, further processing can reduce the capacity as required. For a planar power source configuration (galvanic or electrolytic) measured capacity can be normalized to its x-y area. For example, for a 100 sq. mm. power source electrode measured at an average coulombic capacity of 108 mA-minutes, capacity can be normalized to 1.08 mA-min/sq. mm. In order to adjust that lot of power source electrodes to 100 mA-min, 7.4 sq. mm of each electrode must be removed or otherwise electrically isolated (such as by masking). FIGS. 5A and 5B represents this step for a galvanic power source electrode, where removed areas 70 and 72 serve to reduce the total coulombic capacities of reducible electrode 24 and oxidizable electrode 26, respectively. FIGS. 6A and 6B illustrate adjustment of electrolytic power sources, where removed area 74 is a preselected proportion of total area 76.

Those skilled in the art will recognize that "additive" processing of a lot can be accomplished, using similar calculations but incorporating an additional layer (or layers) of active material appropriately dimensioned and electrically connected. For example, if it is determined that lot capacity falls below that desired, further processing can increase that capacity as required. For example, for a 100 sq. mm. power source electrode measured at an average coulombic capacity of 92 mA-minutes, capacity can be normalized to 0.92 mA-min/sq.mm. In order to adjust that lot of power source electrodes to 100 mA-min, additional material of equivalent to about 0.08 mA-min/sq.mm can be additionally added onto, or otherwise electrically connected to, the existing electrode material.

It will be appreciated that the material of conductors and electrodes may be applied using any appropriate film technology. Thus, material can be added when an electrocapacity is found to be in need of adjustment by the addition of more material.

Figure 7A:
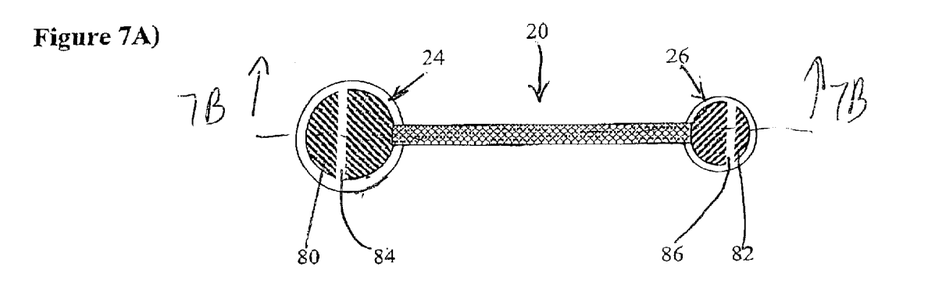
FIGS. 7A and 7B illustrate an alternate embodiment in plan view and cross-sectional view illustrating a different method of galvanic capacity adjustment.
Figure 7B:
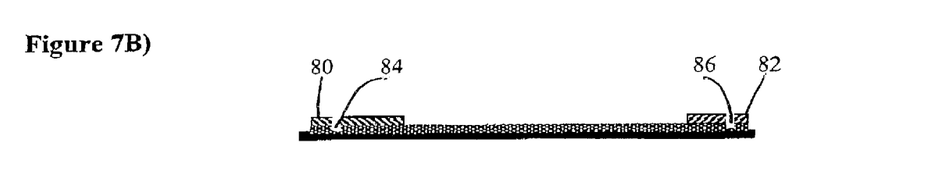

FIG. 7 shows an alternate embodiment of the galvanic power source 20 in which the capacity has been adjusted by the isolation of a fraction 80 of electrode 24 and a fraction 82 of the electrode 26. As was the case in FIG. 5, the fractions 80, 82 represent known portions of the area of each electrode which, when removed from the active electrode area, provide the necessary adjustment in the capacity to bring it into a desired range. The separation gaps 84, 86 extend down to the substrate 22 thereby severing the respective fragments 80, 82 from participation in the galvanic couple.

Figure 8A:
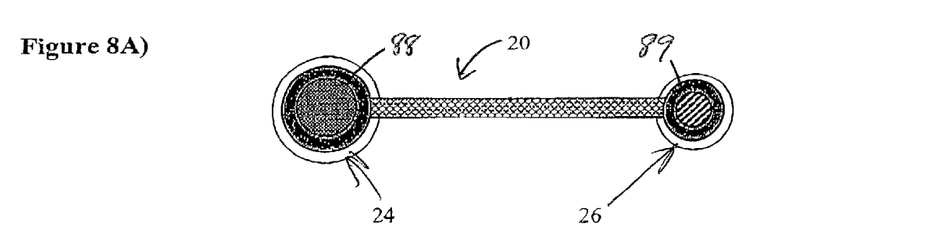
FIGS. 8A and 8B illustrate a plan view and cross-sectional view similar to those in FIGS. 7A and 7B, but illustrating yet another power-limiting or adjusting configuration.
Figure 8B:
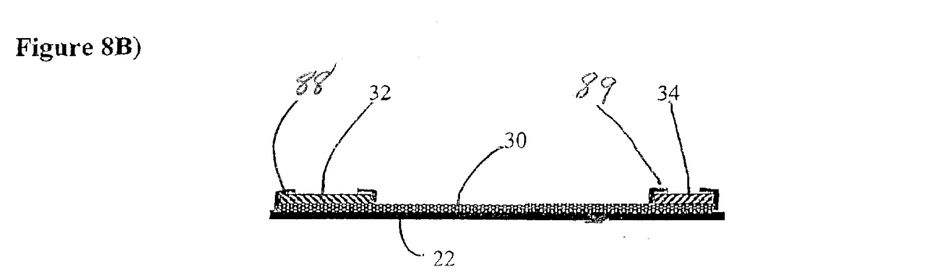

FIGS. 8A and 8B illustrate a galvanic power source 20 after subjection to yet still another technique for capacity adjustment in which a designated portion of the electrodes at 88, 89 has been isolated by masking using a non-conducting over-layer mask. The masked portion of each electrode is isolated as it cannot contact the electrolyte solution when the device is activated for iontophoresis.

FIG. 9 represents an exploded view depicting the assembly of one possible configuration of a wearable iontophoretic patch device utilizing a power source in accordance with the present invention. The patch includes an impervious non-conducting flexible backing layer 90 which can be constructed, for example, using porous elastic polyurethane non-woven type 3M 9907T manufactured by 3M Company of Saint Paul, Minn., or other such material. The backing layer 90 has a smooth bottom or outer surface and the upper or inner surface 92 is provided with a layer of adhesive material to which an impermeable barrier shape 94 which may be, for example, 3M #1526 polyethylene tape is adhered but which leaves a perimeter of exposed adhesive materials surrounding the barrier shape 94 when assembled.

A power source in accordance with the present invention is shown at 96 as a galvanic power source but which, it will be recognized, could also be an electrolytic device. A figure 8-shaped foam barrier is illustrated at 98 which may be 3M #1773 material and which provides a recess for holding a pair of absorbent pads 100 which are in the form of hydrophilic absorbent layers designed to retain electrolyte fluid in contact with the electrodes 102 and 104 of the power source 96 when the device is activated. The hydrophilic layers 100 can be any material which retains an aqueous solution such as, for example, polyacrymalide, cotton, gauze or any other suitable such material. Finally, a release liner also in the form of a FIG. 8 configuration is shown at 106 which, in the assembled patch, releasably adheres to the perimeter of the adhesive layer 92 of the flexible backing layer 90 outside of or beyond the barrier 94 and is designed to be removed when the patch is applied to the skin of a patient.

FIG. 10 represents a schematic diagram of another multiple-cell or multiple-couple embodiment of the power source or battery design of the present invention in an iontophoresis patch shown generally at 110 with release paper liner and absorbent electrolytic pads removed and including an oval section 112 which contains separate oxidizable and reducible species zones 114 and 116 on a substrate (not shown). These are designed to operate as an electrolytic cell couple when an absorbent electrolyte pad (not shown) containing a salt solution is placed over the entire center oval 112. If Zn is the oxidizable species and AgCl is the reducible species, for example, this results in an electrolytic battery or cell that produces one volt. To this is added an additional oxidizable species source 120 connected to reducible source 116 by a conductor 122 and an additional source of reducible material 124 is connected to the source of oxidizable material 114 by another conductor 126. The couple 120–124 represents a galvanic cell that also produces one volt when the oxidizable species is Zn and the reducible species is AgCl. This galvanic cell or couple, of course, is additive with respect to the electrolytic source at 112 resulting in an overall total system that will theoretically produce a two-volt source in which the entire configuration may be contained on a common substrate 118 as previously described. The system also depicts a foam barrier layer 118, impermeable barrier layer 128, and a flexible backing layer 130 which carries an adhesive layer (not shown).

Thus, not only can galvanic and electrolytic couples be utilized separately in power sources adjusted in accordance with the present invention, hybrid power sources that combine both types of cells may be utilized to adjust the desired output voltage of the composite cell or battery. It will also be recognized that a plurality of cells or couples of the same type (galvanic, electrolytic) can also be used. The cells or couples, in any event, may use the same or different species in the couple.

It will be appreciated that by increasing the potential or voltage output of the power source using multiple couples or cells of benign components, the wear time associated with the delivery, of a given mAmin related dose can be greatly reduced. Wear time for a given patch capacity is an important factor to be considered in the use of iontophoretic patches and an ability to deliver a more effective treatment (higher dosage) of a medication or other therapeutic agent safely and in less time using a higher potential represents another advantage. Other configurations of power sources are illustrated and described in U.S. patent application Ser. No. 09/613,984 entitled "RATE ADJUSTABLE DRUG DELIVERY SYSTEM" which is assigned to the same assignee as the present invention and is incorporated herein by reference in its entirety for any purpose.

Dosages of patches of the class typically vary in stepped mAmin increments as 20, 40, etc. With respect to the adjustment of power source charge capacity according to the present invention, any range desired, perhaps plus or minus 10%, or some other amount, may be picked as acceptable limits. Accuracy achieved using the present invention enables many more power sources in a batch to equal or exceed the desired measure of uniformity.

The capacity of each of the elements of the composite system can be adjusted in the same manner as has been previously described for the separate systems. As was the case with earlier galvanic cells or couples, the material of the outer electrodes 120 and 124 is carried on additional amounts of conductors as substrate layers so that the entire amount of material is initially available to the power source.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A galvanic power source comprising:
   (a) an amount of an oxidizable species;
   (b) an amount of a reducible species;
   (c) a common conductor connecting and carrying said amounts of said oxidizable species and said reducible species in separated spaced relation, all of said amounts of said oxidizable species and said reducible species having access to said common conductor thereby forming a pair of totally consumable electrodes; and
   (d) wherein an original amount of at least one of said oxidizable species and said reducible species is altered so as to be within a desired range of amounts by one or more steps selected from the group consisting of physical addition, physical removal and separation by isolation of a portion of said original amount.

2. A galvanic power source as in claim 1 wherein said conductor comprises a layer of material carried on a flexible substrate.

3. A galvanic power source as in claim 1 wherein said electrodes are formed as layers of generally known thickness and area on said common conductor.

4. A galvanic power source as in claim 2 wherein said electrodes are formed as layers of generally known thickness and area on said common conductor.

5. A galvanic power source as in claim 4 including a central opening in one or both of said electrodes.

6. A galvanic power source as in claim 5 including a central opening in both of said electrodes.

7. A galvanic power source as in claim 4 wherein a portion of the area of at least one of said electrodes is electrically isolated from said common conductor.

8. A galvanic power source as in claim 7 wherein a portion of the area of both of said electrodes is electrically isolated from said common conductor.

9. A galvanic power source as in claim 4 including a shield layer coating a portion of the area of at least one of said electrodes to preclude contact with an electrolyte contacting the electrode in the portion of the area covered by said shield layer.

10. A galvanic power source as in claim 9 including a shield layer coating a portion of the area of both of said electrodes to preclude contact with an electrolyte contacting either electrode in the portion of the area covered by said shield layer.

11. A galvanic power source as in claim 4 wherein at least one of said electrodes is provided with a discontinuity extending to said substrate thereby electrically isolating a portion of its area from said common conductor.

12. A galvanic source as in claim 11 wherein both of said electrodes are provided with a discontinuity extending to said substrate thereby electrically isolating a portion of their areas from said common conductor.

13. A galvanic power source as in claim 4 including an additional layer of electrode material on one or both of said electrodes.

14. A galvanic power source as in claim 13 including an additional layer of electrode material on both of said electrodes.

15. An electrolytic power source comprising:
 (a) an amount of an oxidizable species;
 (b) an amount of a reducible species;
 (c) a common ionic conductor connecting said amounts of said oxidizable species and said reducible species, all of said amounts of said oxidizable species and said reducible species having access to said common ionic conductor thereby forming a pair of totally consumable electrodes; and
 (d) wherein an original amount of one or more of said oxidizable species and said reducible species is adjusted to an amount within a desired range by one or more steps selected from the group consisting of physical addition, physical removal and separation by isolation of a portion of said original amount.

16. An electrolytic power source as in claim 15 wherein said conductor comprises a layer of material carried on a flexible substrate.

17. An electrolytic power source as in claim 15 wherein said electrodes are formed as layers of generally known thickness and area on said common conductor.

18. An electrolytic power source as in claim 16 wherein said electrodes are formed as layers of generally known thickness and area on said common conductor.

19. An electrolytic power source as in claim 18 including a central opening in at least one of said electrodes.

20. An electrolytic power source as in claim 19 wherein both of said electrodes are provided with a central opening.

21. An electrolytic power source as in claim 18 wherein a portion of the area of at least one of said electrodes is electrically isolated from said common conductor.

22. An electrolytic power source as in claim 21 wherein a portion of the original area of both of said electrodes is electrically isolated from said common conductor.

23. An electrolytic power source as in claim 18 including a shield layer coating a portion of the area of at least one of said electrodes to preclude contact with an electrolyte contacting the electrode in the portion of the area covered by said shield layer.

24. An electrolytic power source as in claim 23 including a shield layer coating a portion of the area of both of said electrodes to preclude contact with an electrolyte contacting either electrode.

25. An electrolytic power source as in claim 18 wherein at least one of said electrodes has a portion of its area electrically isolated from said common conductor by provision of a discontinuity extending to said substrate.

26. An electrolytic source as in claim 25 wherein both of said electrodes have a portion of their areas electrically isolated from said common conductor by provision of a discontinuity extending to said substrate.

27. An electrolytic power source as in claim 18 including an additional layer of a known amount of electrode material on one or both of said electrodes.

28. An electrolytic power source as in claim 27 wherein an additional layer of known amount of electrode material is added to both of said electrodes.

29. An electrolytic power source comprising:
 (a) one or more amounts of an oxidizable species;
 (b) one or more amounts of a reducible species;
 (c) an ionic conductor serially connecting said one or more amounts of said oxidizable species and said one or more amounts of said reducible species, all of said amounts of said oxidizable species and said reducible species having access to an ionic conductor; and
 (d) wherein an original amount of one or more of said oxidizable species and said reducible species are adjusted to amounts within a desired range by physical removal of a portion of said layered construction of known area.

30. A method for adjusting the capacity of an electrochemical power source having an initial amount of an oxidizable material and an initial amount of a reducible material, wherein said initial amount of at least one of said oxidizable and said reducible materials has a target charge capacity range, comprising the step of altering the initial amount of at least one of said oxidizable material and said reducible material available to participate in said power source when necessary to conform the charge capacity to said target range by one or more techniques selected from the group consisting of adding, removing, isolating and shielding a known fraction of said initial amount.

31. A method of claim 30 wherein said power source includes a plurality of amounts of oxidizable material and reducible material.

32. A method as in claim 30 wherein said electro-chemical power source is manufactured as part of a lot of power sources and further comprising the steps of:
 (a) sampling said lot by removing one or more test power sources from said lot;
 (b) measuring the amount of at least one of said oxidizing material and said reducible material contained in said test power source;
 (c) comparing said measured amount with said target amount;
 (d) if said target amount differs sufficiently from said measured amount, noting the fraction of said measured amount by which it differs from said target amount; and
 (e) utilizing the fractional difference measured to determine an amount by which to alter the initial amount of one or both of said oxidizable material and said reducible material to adjust corresponding total charge capacity in said power sources in some or all of the remainder of said lot of power sources.

33. A method as in claim 32 wherein the amount of both said oxidizing material and said reducible material contained in said test power source are measured.

34. A method as in claim 32 wherein the amount of said material is measuring the total charge capacity to exhaustion.

35. A method as in claim 33 wherein the amount of said material is measured by measuring the total charge capacity to exhaustion.

36. A method as in claim 32 wherein said oxidizable species and said reducible species are formed as coatings of predetermined thickness and area on a conductive substrate and wherein said amount is altered by removal of part of said area including said substrate.

37. A method as in claim 32 wherein said oxidizable species and said reducible species are formed as coatings of predetermined thickness and area on a conductive substrate and including the step of altering the initial amount of one or both of said oxidizable material and said reducible by isolating a portion of said area.

38. A method as in claim 37 wherein said portion of said area is isolated by creating a discontinuity between a portion of the area and said conductor.

39. A method as in claim 37 wherein said isolation step includes masking a portion of said area to preclude electrolyte contact with it.

40. A method as in claim 32 wherein said oxidizable species and said reducible species are formed as coatings of predetermined thickness and area on a conductive substrate and including the step of altering the initial amount of one or both of said oxidizable material and said reducible material by adding material to one or both of said coatings.

41. A method as in claim 39 wherein material is added to both said coatings.

42. A method as in claim 32 wherein said oxidizable species and said reducible species are formed as coatings of predetermined thickness and area on a conductive substrate by a screen printing process and wherein said amount is altered by addition of material to one or both of said oxidizable species and said reducible species by an additional screen printing step.

43. A method as in claim 30 including the step of adding material to both said coatings.

44. A method as in claim 30 wherein a plurality of techniques are employed.

45. A method as in claim 43 including the steps of adding an amount of one or more of said oxidizable species and said reducible species to adjust the total amount to be within a desired range followed by a reduction of a known amount of the material to adjust the charge capacity of said electrochemical power source.

46. An electrochemical power source comprising:
(a) one or more amount of oxidizable species;
(b) one or more amounts of reducible species;
(c) one or more conducting media connecting said amounts of said oxidizable species and said reducible species, all of said amounts of said oxidizable species and said reducible species having access to a conducting medium; and
(d) wherein at least one original amount of said one or more oxidizable species and said one or more reducible species has been altered to adjust the charge capacity of said power source.

47. An electrochemical power source as in claim 46 including a plurality of amounts of oxidizable species and a plurality of amounts of reducible species connected by a plurality of conducting media.

48. An electrochemical power source as in claim 46 wherein said electrochemical power source includes both galvanic and electrolytic couples.

49. An electrochemical power source as in claim 47 wherein said electrochemical power source includes both galvanic and electrolytic couples.

50. An electrochemical power source comprising:
(a) an amount of an oxidizable species;
(b) an amount of a reducible species;
(c) a common conducting medium connecting said amounts of said oxidizable species and said reducible species, all of said amounts of said oxidizable species and said reducible species having access to said conducting medium; and
(d) wherein an original amount of one or more of said oxidizable species and said reducible species has been adjusted by a technique selected from the group consisting of addition, removal, isolation or shielding of a known amount of material to adjust the charge capacity of said electrochemical power source.

51. A wearable, disposable iontophoretic delivery device including a power source as in claim 46.

52. A device as in claim 51 wherein said electrochemical power source includes a plurality of amounts of oxidizable species and a plurality of amounts of reducible species connected by a plurality of conducting media.

53. A device as in claim 51 wherein said electrochemical power source includes both galvanic and electrolytic couples.

54. A device as in claim 51 wherein the original amount of one or more of said oxidizable species and said reducible species has been adjusted by a technique selected from the group consisting of addition, removal, isolation or shielding of a known amount of material to adjust the charge capacity of said electrochemical power sources.

55. A method as in claim 30 including the step of physically removing a portion of original area of at least one of said electrodes to adjust corresponding total charge capacity.

56. A galvanic power source as in claim 55 including the step of physically removing a portion of original area of both of said electrodes to adjust corresponding total charge capacity.

57. A method as in claim 30 wherein said oxidizable species and said reducible species are of a layered construction formed as coatings of known thickness and area on substrates and wherein said amounts of said oxidizable and reducible species are adjusted by removal of a portion of said layered construction.

58. A galvanic power source comprising:
(a) an amount of an oxidizable species;
(b) an amount of a reducible species;
(c) a common conductor comprising a layer of material carried on a flexible substrate, said common conductor carrying said amounts of said oxidizable species and said reducible species as coatings on said common conductor in separated spaced relation.

59. An electrolytic power source comprising:
(a) an amount of an oxidizable species;
(b) an amount of a reducible species;
(c) a common ionic conductor comprising a layer of material carried on a flexible substrate, said common conductor carrying said amounts of said oxidizable species and said reducible species as coatings on said common conductor in seperated spaced relation.

* * * * *